United States Patent
Isaac et al.

(10) Patent No.: US 12,030,055 B2
(45) Date of Patent: Jul. 9, 2024

(54) MICROFLUIDIC ANALYTICAL DEVICE

(71) Applicant: LIGHTCAST DISCOVERY LTD, Cambridge (GB)

(72) Inventors: Thomas Henry Isaac, Cambridge (GB); Pedro Cunha, Cambridge (GB); Eoin Sheridan, Cambridge (GB); David Love, Cambridge (GB); Rebecca Palmer, Cambridge (GB); Douglas J Kelly, Cambridge (GB); Gareth Podd, Cambridge (GB)

(73) Assignee: LIGHTCAST DISCOVERY LTD, Cambridge (GB)

( * ) Notice: Subject to any disclaimer, the term of this patent is extended or adjusted under 35 U.S.C. 154(b) by 281 days.

(21) Appl. No.: 17/708,342

(22) Filed: Mar. 30, 2022

(65) Prior Publication Data

US 2022/0219173 A1    Jul. 14, 2022

Related U.S. Application Data

(62) Division of application No. 16/625,094, filed as application No. PCT/EP2018/066574 on Jun. 21, 2018, now Pat. No. 11,318,472.

(30) Foreign Application Priority Data

Jun. 21, 2017  (EP) ..................................... 17177204
Jul. 7, 2017   (EP) ..................................... 17180391

(51) Int. Cl.
   *B01L 3/00*       (2006.01)
   *C12Q 1/6869*     (2018.01)

(52) U.S. Cl.
   CPC ...... *B01L 3/502792* (2013.01); *C12Q 1/6869* (2013.01); *B01L 2200/0673* (2013.01);
   (Continued)

(58) Field of Classification Search
   CPC ..... B01L 2200/0673; B01L 2300/0864; B01L 2300/0887; B01L 2300/089;
   (Continued)

(56) References Cited

U.S. PATENT DOCUMENTS 4,962,020 A   10/1990  Tabor et al.
6,565,727 B1  5/2003   Shenderov
(Continued)

FOREIGN PATENT DOCUMENTS

EP  2 828 408   10/2015
EP  3 150 725   4/2017
(Continued)

OTHER PUBLICATIONS

Vasanthsekar Shekar et al., "Towards Automated Optoelectrowetting on Dielectric Devices for Multi-Axis Droplet Manipulation", 2013 IEEE International Conference on Robotics and Automation (ICRA), Karlsruhe, Germany, May 6-10, 2013, pp. 1439-1445.
(Continued)

*Primary Examiner* — Sunghee Y Gray
(74) *Attorney, Agent, or Firm* — Wenderoth, Lind & Ponack, L.L.P.

(57) ABSTRACT

A device comprising: a first zone comprising an attachment site; a first pathway; a second pathway and a means for creating a second medium comprised of aqueous microdroplets in a carrier; a microdroplet manipulation zone comprising: a first composite wall comprised of a first transparent substrate; a first transparent conductor layer on the substrate; a photoactive layer activated by electromagnetic radiation; and a first dielectric layer on the photoactive layer; a second composite wall comprised of a second substrate; a second conductor layer on the substrate; and optionally a second dielectric layer on the conductor layer; an A/C source; a source of first electromagnetic radiation; means for manipu-
(Continued)

lating the points of impingement of the electromagnetic radiation on the photoactive layer; an detection zone disposed downstream of the microdroplet manipulation zone or integral therewith; and a fluorescence or Raman-scattering detection system.

9 Claims, 2 Drawing Sheets

(52) U.S. Cl.
CPC .............. *B01L 2300/0864* (2013.01); *B01L 2300/0887* (2013.01); *B01L 2300/089* (2013.01); *B01L 2300/165* (2013.01); *B01L 2300/168* (2013.01); *B01L 2400/0427* (2013.01)

(58) Field of Classification Search
CPC ......... B01L 2300/161; B01L 2300/165; B01L 2300/168; B01L 2400/0427; B01L 3/502792; C12Q 1/6869; F28D 1/0333
USPC ........................................................ 356/409
See application file for complete search history.

(56) References Cited

U.S. PATENT DOCUMENTS

| | | |
|---|---|---|
| 2003/0224528 A1 | 12/2003 | Chiou et al. |
| 2006/0194331 A1 | 8/2006 | Pamula et al. |
| 2007/0062583 A1 | 3/2007 | Cox |
| 2007/0138016 A1 | 6/2007 | Wang |
| 2007/0241068 A1 | 10/2007 | Pamula et al. |
| 2008/0281471 A1 | 11/2008 | Smith |
| 2009/0155902 A1 | 6/2009 | Pollack et al. |
| 2010/0096266 A1 | 4/2010 | Kim et al. |
| 2011/0147215 A1 | 6/2011 | Fuchs et al. |
| 2012/0044299 A1 | 2/2012 | Winger |
| 2012/0091003 A1 | 4/2012 | Chuang et al. |
| 2013/0143312 A1 | 6/2013 | Wheeler et al. |
| 2013/0233425 A1 | 9/2013 | Srinivasan et al. |
| 2013/0293246 A1 | 11/2013 | Pollack et al. |
| 2015/0027889 A1 | 1/2015 | Pollack et al. |
| 2015/0174578 A1 | 6/2015 | Srinivasan et al. |
| 2015/0247192 A1 | 9/2015 | Frayling et al. |
| 2015/0253284 A1 | 9/2015 | Sudarsan et al. |
| 2015/0298125 A1 | 10/2015 | Ermakov |
| 2016/0102280 A1 | 4/2016 | Tovar et al. |
| 2016/0158748 A1 | 6/2016 | Wu et al. |
| 2016/0160259 A1 | 6/2016 | Du |
| 2017/0043343 A1 | 2/2017 | Khandros et al. |
| 2017/0080428 A1 | 3/2017 | Shenderov |
| 2017/0121675 A1 | 5/2017 | Sugarman |
| 2017/0173580 A1 | 6/2017 | Lowe, Jr. et al. |
| 2017/0175179 A1 | 6/2017 | Hiddessen et al. |
| 2018/0008985 A1 | 1/2018 | Balmforth |
| 2018/0111126 A1 | 4/2018 | Osmus |
| 2018/0133715 A1 | 5/2018 | Craig et al. |
| 2018/0313819 A1 | 11/2018 | Pugia et al. |

FOREIGN PATENT DOCUMENTS

| | | | |
|---|---|---|---|
| JP | 2005-531409 | 10/2005 | |
| JP | 2010-503516 | 2/2010 | |
| KR | 20130064512 | * 6/2013 | ............. G01N 37/00 |
| WO | 2004/012848 | 2/2004 | |
| WO | 2008/051310 | 5/2008 | |
| WO | 2010/151794 | 12/2010 | |
| WO | 2014/053853 | 4/2014 | |
| WO | 2014/053854 | 4/2014 | |
| WO | 2014/111723 | 7/2014 | |
| WO | 2014/167323 | 10/2014 | |
| WO | 2014/167324 | 10/2014 | |
| WO | 2016/116757 | 7/2016 | |
| WO | 2018/042028 | 3/2018 | |
| WO | 2018/046521 | 3/2018 | |
| WO | 2018/054964 | 3/2018 | |
| WO | 2018/234445 | 12/2018 | |
| WO | 2018/234446 | 12/2018 | |

OTHER PUBLICATIONS

Shao Ning Pei et al., "Distributed Circuit Model for Multi-Color Light-Actuated Opto-Electrowetting Microfluidic Device", Journal of Lightwave Technology, 2015, vol. 33, No. 16, pp. 3486-3493.
Aldrich N. K. Lau et al., "Antifouling coatings for optoelectronic tweezers", Lab Chip, 2009, vol. 9, pp. 2952-2957.
Chiou et al., "Continuous optoelectrowetting for picoliter droplet manipulation", Applied Physics Letters, 2008, vol. 93, No. 22, pp. 221110-1-221110-3.
Pei, "Optofluidic Devices for Droplet and Cell Manipulation", Electronic Theses and Dissertations, 2015, 107 pages.
Park et al., "Single-sided continuous optoelectrowetting (SCOEW) for droplet manipulation with light patterns", Lab on a Chip, 2010, vol. 10, No. 13, pp. 1655-1661.
Valley et al., "A unified platform for optoelectrowetting and optoelectronic tweezers", Lab on a Chip, 2011, vol. 11, No. 7, pp. 1292-1297.
Deutscher et al., "Enzymatic Synthesis of Deoxyribonucleic Acid", The Journal of Biological Chemistry, 1969, vol. 244, No. 11, pp. 3019-3028, XP055447222.
Zhou et al., "Electrostatic charging and control of droplets in microfluidic devices", Lab on a Chip, 2013, vol. 13, No. 5, pp. 962-969.
Chiou et al., "Pico liter droplet manipulation based on a novel continuous opto-electrowetting mechanism", 12th International Conference on Transducers, Solid State Sensors, Actuators and Microsystems, 2003, vol. 1, pp. 468-471.
Jing et al., "Jetting microfluidics with size-sorting capability for single-cell protease detection", Biosensors and Bioelectronics, 2014, vol. 66, pp. 19-23.
Ng et al., "Digital Microfluidic Cell Culture", Annual Review of Biomedical Engineering, 2015, vol. 17, No. 1, pp. 91-112.
Barbulovic-Nad et al., "A microfluidic platform for complete mammalian cell culture", Lab on a Chip, 2010, vol. 10, No. 12, pp. 1536-1542.
Eydelnant et al., "Virtual microwells for digital microfluidic reagent dispensing and cell culture", Lab on a Chip, 2012, vol. 12, pp. 750-757.
Park et al., "On-chip characterization of cryoprotective agent mixtures using an EWOD-based digital microfluidic device", Lab on a Chip, 2011, vol. 11, No. 13, pp. 2212-2221.
Huang et al., "Fertilization of Mouse Gametes in Vitro Using a Digital Microfluidic System", IEEE Transactions on Nanobioscience, 2015, vol. 14, No. 8, pp. 857-863.
Huang et al., Digital Microfluidic Dynamic Culture of Mammalian Embryos on an Electrowetting on Dielectric (EWOD) Chip, Plos One, 2015, vol. 10, No. 5, 15 pages.
International Search Report dated Jul. 19, 2018 in International (PCT) Patent Application No. PCT/EP2018/066574.

* cited by examiner

MICROFLUIDIC ANALYTICAL DEVICE

This invention relates to a device for investigating a nucleic acid molecule; in particular a device for sequencing DNA or RNA either of natural or synthetic origin.

In our previous applications WO 2014/053853, WO 2014/053854, WO2014/167323, WO2014/167324 and WO2014/111723, we have described a new sequencing method which involves progressive digestion of a polynucleotide analyte to generate an ordered stream of single nucleotides, preferably a stream of single nucleoside triphosphates, each of which can be captured one-by-one into corresponding microdroplets in a microdroplet stream. Thereafter, each droplet can be chemically and/or enzymatically manipulated to reveal the particular single nucleotide it originally contained. In one embodiment, these chemical and/or enzymatic manipulations comprise a method involving the use of one or more two-component oligonucleotide probe types each of which is adapted to be able to selectively capture one of the single nucleotide types from which the analyte is constituted. Typically, in each of such probe types, one of the two oligonucleotide components comprises characteristic fluorophores and in the probe's unused state the ability of these fluorophores to fluoresce remains extinguished by virtue of the presence of quenchers located close-by or by self-quenching. In use, when the probe has captured its corresponding single nucleotide, it is rendered susceptible to subsequent exonucleolysis or endonucleolysis thereby liberating the fluorophores from the quenchers and/or each other enabling them to fluoresce freely. By this means, the original single nucleotide present in each droplet can be inferred indirectly by spectroscopic means.

In designing sequencing devices it is necessary to manipulate many thousands of microdroplets ensuring for example that they can be reliably delivered to locations where they can be merged with other and/or their contents analysed for the presence or absence of fluorescence.

One possible way in doing this is to establish pathways on a substrate along which the microdroplets can be propelled by electrowetting forces. Devices for manipulating relatively large droplets in this way have been previously described in the art; see for example U.S. Pat. No. 6,565,727, US20130233425 and US20150027889. Typically, this is achieved by causing the droplets, for example in the presence of an immiscible carrier fluid, to travel through a microfluidic channel defined by two opposed walls of a cartridge or tubing. Embedded in the walls of the cartridge or tubing are electrodes covered with a dielectric layer each of which are connected to an A/C biasing circuit capably of being switched on and off rapidly at intervals to modify the electrowetting characteristics of the layer. This gives rise to localised directional capillary forces that can be used to steer the droplet along a given path.

A variant of this approach, based on optically-mediated electrowetting, has been taught in for example US20030224528, US20150298125 and US20160158748. In particular, the first of these three patent applications discloses various microfluidic devices which include a microfluidic cavity defined by first and second walls and wherein the first wall is of composite design and comprised of substrate, photoconductive and insulating (dielectric) layers. Between the photoconductive and insulating layers is disposed an array of conductive cells which are electrically isolated from one another and coupled to the photoactive layer and whose functions are to generate corresponding discrete droplet-receiving locations on the insulating layer. At these locations the surface tension properties of the droplets can be modified by means of electrowetting forces. The conductive cells may then switched on and off by light impinging on the photoconductive layer. This approach has the advantage that switching is made much easier and quicker although its utility is to some extent still limited by the arrangement of the electrodes. Furthermore, there is a limitation to the speed at which droplets can be moved and the extent to which the actual droplet pathway can be varied.

A double-walled embodiment of this latter approach has been disclosed in University of California at Berkeley thesis UCB/EECS-2015-119 by Pei. Here, a cell is described which allows the manipulation of relatively large droplets in the size range 100-500 μm using optical electrowetting across a surface of Teflon AF deposited over a dielectric layer. A light-pattern over un-patterned electrically biased amorphous silicon is described in schematic form. However, in the scheme shown the dielectric layer is thin (100 nm) and disposed only on the wall bearing the photoactive layer.

We have now developed a nucleic acid investigative device which is capable of manipulating many thousands of microdroplets simultaneously in accordance with the requirements of a reliable single nucleotide detection method. It has the advantage of being easily reconfigurable by the application of computer software making it very versatile; for example by allowing the user to readily adapt it for optimum accuracy, throughput or detecting particular epigenetic modifications. Thus according to the present invention there is provided a device for investigating a nucleic acid analyte characterised by comprising:

a first zone comprising an attachment site to which the analyte is attached; a first pathway for causing a first fluid medium to flow over the attachment site thereby allowing the nucleic acid to be progressively pyrophosphorolysed into its constituent nucleoside triphosphates; a second pathway for removing the nucleoside triphosphates from around the attachment site and a means for creating in the second pathway a second medium comprised of aqueous microdroplets in a water-immiscible carrier;

a microdroplet manipulation zone for manipulating the microdroplets using optically-mediated electrowetting comprised of:

a first composite wall comprised of
  a first transparent substrate;
  a first transparent conductor layer on the substrate having a thickness in the range 70 to 250 nm;
  a photoactive layer activated by electromagnetic radiation in the wavelength range 400-1000 nm on the conductor layer having a thickness in the range 300-1000 nm and
  a first dielectric layer on the photoactive layer having a thickness in the range 120 to 160 nm;

a second composite wall comprised of
  a second substrate;
  a second transparent conductor layer on the substrate having a thickness in the range 70 to 250 nm and
  optionally a second dielectric layer on the conductor layer having a thickness in the range 25 to 50 nm;
  wherein the exposed surfaces of the first and second dielectric layers are disposed less than 10 μm apart to define a microfluidic space adapted to contain microdroplets;

an A/C source to provide a potential difference across the first and second composite walls connecting the first and second conductor layers;

at least one source of first electromagnetic radiation having an energy higher than the bandgap of the photoexcitable layer adapted to impinge on the photoactive layer to induce corresponding ephemeral first electrowetting locations on the surface of the first dielectric layer;

means for manipulating the points of impingement of the electromagnetic radiation on the photoactive layer so as to vary the disposition of the ephemeral electrowetting locations thereby creating at least one first electrowetting pathway along which the microdroplets may be caused to move;

an detection zone disposed downstream of the microdroplet manipulation zone or integral therewith and a fluorescence or Raman-scattering detection system comprising a source of second electromagnetic radiation adapted to impinge on the microdroplets in the detection zone and a detector for detecting fluorescence or Raman-scattering emitted therefrom.

The device of the present invention is especially suitable for analysing the constituent nucleotides of a nucleic acid analyte and in one embodiment is a device for sequencing DNA or RNA. In applications where the nucleic acid analyte DNA, it is suitably a double-stranded polynucleotide and may have a nucleotide chain length which can in principle be unlimited; for example up to and including the many millions of nucleotide base pairs found in a fragment of a genome. In one embodiment, the analyte will therefore be at least 50, preferably at least 150 nucleotide base pairs long; suitably it will be greater than 500, greater than 1000 and in some cases 5000+ nucleotide base pairs long. In one embodiment, the analyte is DNA of natural origin (e.g. genetic material derived from a plant, animal, bacterium or a virus) although the method is equally applicable to the sequencing of partially or wholly synthetic DNA or indeed other nucleic acids made up wholly or in part of nucleotides comprised of nucleotide bases that are not commonly encountered in nature; i.e. nucleotides having nucleobases other than adenine, thymine, guanine, cytosine and uracil. Examples of such nucleobases include 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine. Where the analyte is RNA similar considerations will apply.

In the first zone of the device, the analyte is progressively pyrophosphorolysed, in the 3-5' direction to generate a stream of single nucleoside triphosphates the order of which corresponds to that of the sequence of the analyte. The pyrophosphorolysis itself is generally carried out at a temperature in the range 20 to 90° C. in the presence of a reaction medium including an enzyme such as a polymerase. Suitably, it is carried out so that the single nucleoside triphosphates are continually removed from the region of pyrophosphorolysis around the particle by a flowing fluid medium which is aqueous. In one embodiment, this medium is buffered and also contains those other components needed to sustain the pyrophosphorolysis reaction (polymerase, pyrophosphate anion, magnesium cation etc.). In another embodiment, the medium additionally contains one or more of (a) the probe types specified in our earlier patent applications (or probes having an equivalent function); (b) the various chemicals and enzymes required to cause the probe to bind to and capture the relevant single nucleoside triphosphate (e.g. polymerase and/or ligase) and (3) an enzyme required to cause subsequent exonucleolysis of the used probe to occur. In one embodiment, some or all of these components are introduced together or in stages into the flowing aqueous medium or the microdroplets formed therefrom (as the case may be) at some other point(s) or zone(s). For example, subsequent introduction of some or all of these components directly into the microdroplets can be achieved by injection using an injector or by microdroplet coalescence.

Preferably the device is designed to be operable so that the rate of pyrophosphorolysis is as fast as possible and in one embodiment this rate lies in the range from 1 to 50 single nucleoside triphosphates per second. Further information about the pyrophosphorolysis reaction as applied to the progressive degradation of polynucleotides can be found for example in J. Biol. Chem. 244 (1969) pp. 3019-3028.

The first zone of the device is in part characterised by including an attachment site which is adapted to bind to the analyte. In one embodiment, this site is adapted to bind temporarily to a particle having two different surface regions. Suitably, it comprises a surface located within the first zone which is modified to be releasably attachable to a corresponding particle bearing a molecule of the analyte; for example via a chemically-modified metal coating. In one embodiment, this particle comprises a bead; for example a microbead, made of an inert material such as glass, silica, alumina, a metal or a non-degradable polymer. In another embodiment, the particle has a core of paramagnetic material enabling it to be manipulated magnetically.

The two different surface regions on the particle are adapted to bind to complementary sites on the attachment site and the analyte respectively. In one embodiment, the first of these regions is comprised of a chemically-modified metal coating; for example, a functionalised coating of gold, silver, copper or other metal. In another embodiment, the second of these regions is comprised of one or more reactive sites on the particle specifically adapted to bind physically or chemically to a molecule of the analyte.

There are many ways in which the reactive sites on the particle and attachment site can be created. For example, in the case of the first region on the particle, it can be prepared by first partially coating the particles with metal using a known method such as metal vapour deposition, atomic layer deposition, plasma deposition or the like. Thereafter, the metal surface can be chemically modified to introduce one or more first moieties which can reversibly bind to complementary second moieties on the attachment site. In one embodiment, these pairs of first and second moieties are chosen so that the bond created between them can be reversibly made and broken at ambient or near ambient temperatures. By this means, the bead can be attached to the attachment site, the analyte digested by pyrophosphorolysis and thereafter the bead detached from the substrate enabling the latter to then receive another fresh bead. In one embodiment, these pairs of first and second moieties can lead to the formation of protein complexes stable under the conditions of pyrophosphorolysis e.g. by using avidin or streptavidin moieties with complementary biotin moieties. In another, these pairs can create a labile chemical bond; as for example in a polyhistidine/chelated metal ion pair (bond broken at low pH or in the presence of imidazole or strong metal chelator); a boronic acid/suitable carbohydrate pair (bond broken at low pH) or a maleimido/selenol pair (bond broken using meta-chloroperoxybenzoic acid). In these cases, the particle can be subsequently detached by modifying the pH or composition of the aqueous medium flowing through the first zone. Thus in one embodiment of the device the first zone further includes means for introducing and removing the particle from the first zone or means for introducing and removing a particle-detaching means thereinto as further explained below. In another, upon detachment the particle is removed from the attachment site suspended in its own microdroplet which passes through the rest of the device. If this approach is employed then in one embodiment the particle will includes its own characteristic fluorescence or Raman-scattering marker enabling the user to detect when pyrophosphorolysis is complete.

In one preferred embodiment, the pair of moieties mentioned above comprises a polyhistidine moiety comprised of a plurality of histidine residues (preferably greater than six) and a chelator moiety selected from for example a nitrotriacetate (NTA) or iminodiacetate (IDA) salt derivative of a transition metal such as cobalt, copper or nickel. It will be appreciated that these first and second moieties can be deployed on the particle and attachment site respectively either way around.

Likewise, in the case of the particle's second region, there are many ways in which the analyte-reactive sites can be created. Thus, in one embodiment an uncoated surface of the particle may be primed with a functionalising agent, for example in the case of a silica, alumina or glass bead, an epoxysilane, an aminohydrocarbylsilane or a mercaptosilane, to create chemically reactive sites to which the analyte can be attached. Thereafter these reactive sites can be treated with a derivative of the analyte which has been correspondingly modified to include a terminal primer-reactive group; for example in one embodiment an amine, succinyl or thiol group. In another embodiment, chemical attachment can take place via ligation to adaptor oligonucleotides or via the types of protein complexes described above.

In yet another embodiment, the particle so primed will comprise a second region having only one analyte-reactive site so that only one molecule of the analyte can be attached. This can be important if the analyte is a small polynucleotide fragment since otherwise multiple molecules tend to become attached during preparation which is undesirable. It is of a lesser concern if the polynucleotide fragment is large since steric effects will work to militate against such an outcome. Suitably, the particle will have a maximum diameter in the range 0.5 to 5 microns (µm).

In one preferred embodiment, the particles are spherical beads and the first and second regions comprise hemispherical regions abutting one another on the surface. In this embodiment, the particle is suitably a bead having a magnetic core; for example those sold under the name Dynabeads®.

In the case of an embodiment where the bead has a magnetic core, it can be attached and detached from the degradation site using a magnetic field induced from an electromagnet of a permanent magnet placed in the vicinity of the sequencing device.

The first zone is suitably a chamber of microfluidic dimensions containing a structure including the attachment site or, in another embodiment, comprises a microfluidic tube whose internal surface has in part been coated with the attachment site. In one embodiment the attachment site may further include a seating into which the particle can be close-fitted. In another embodiment, the particle may be held in place at the desired location by surface-binding or magnetically. In yet another embodiment the particles may have, for example, a ferromagnetic core or surface enabling them to be guided to the attachment site by application of an electromagnet in close proximity thereto. In yet another embodiment, the particle is located and removed from the attachment site by applying capillary forces to it using conventional or optically-mediated electrowetting on device (EWOD) techniques. Thus, in one embodiment, the first zone further includes dielectric-coated electrodes or photoactive elements (which may be permanent or ephemeral) in the chamber or tubing which may be activated for this purpose as necessary.

In one embodiment the device further includes a preparation zone located upstream of the first zone in which the bead is prepared and means for moving the bead from the preparation zone to the attachment site by means of a second electrowetting pathway.

After pyrophosphorolysis, a flowing second fluid medium, for example a second aqueous medium, containing the single nucleoside triphosphates separated spatially and temporally from each other and arranged in an order corresponding to that of the nucleotide sequence of the analyte is removed from around the attachment site. In one embodiment the pyrophosphorolytic degradation takes place in a continuous stream of first fluid medium which is subsequently dropletised, causing the encapsulation of the nucleoside triphosphate molecule which was previously in the second fluid medium.

In another embodiment, the pyrophosphorolytic degradation takes place in a transient manner in a dropletised first fluid medium in which microdroplets suspended in an immiscible carrier medium temporarily wet and de-wet the target bead as they are driven over its surface. Thus, if a nucleoside triphosphate molecule is released from the DNA strand when the droplet is in contact with the bead, it will be immediately encapsulated and then removed downstream in the second fluid medium when the microdroplet de-wets from the bead.

It will be appreciated that this microdroplet wetting/de-wetting methodology will have application beyond sequencing if the progressive chemical transformation carried out on the analyte is other than pyrophosphorolysis. Thus, according to a second aspect of the present invention there is provided a general method for carrying out a chemical transformation of a target molecule immobilised at a given location characterised by the steps of (a) generating a stream of microdroplets each comprised of a medium capable of causing the chemical transformation to occur; (b) contacting each microdroplet in turn with the target molecule at the given location and for a given period of time under conditions where the chemical transformation can occur and (c) at the end of the given period removing the microdroplet from the given location. In one embodiment, the chemical transformation is pyrophosphorolysis of the type described above and a third aspect comprises provided a method for carrying out pyrophosphorolysis of a target polynucleotide immobilised at a given location characterised by the steps of (a) generating a stream of aqueous microdroplets each comprised of a pyrophosphorolysing medium; (b) contacting each microdroplet in turn with the target polynucleotide at the given location and for a given period of time under conditions where pyrophosphorolysis can occur and (c) at the end of the given period removing the microdroplet from the given location. In this embodiment at least some of the microdroplets removed in step (c) will contain a single nucleoside triphosphate derived from the target polynucleotide which is immobilised at the given location by any of the means described above. In another the microdroplets removed will correspond to an ordered stream of nucleoside triphosphates corresponding to the nucleotide sequence of target. Suitably, the microdroplets are suspended in an immiscible carrier of the type described herein.

In yet another embodiment, the second fluid medium is aqueous and delivered to a second zone where it is then converted into a corresponding stream of aqueous microdroplets; at least some of which contain a single nucleoside triphosphate molecule. In one embodiment, this is achieved by causing the second aqueous medium to issue forth from a microdroplet droplet-generating head of suitable dimensions and geometry into a flowing carrier medium comprising an immiscible liquid such as a hydrocarbon, fluorocarbon or silicone oil.

To avoid the risk that a given microdroplet contains more than one single nucleoside triphosphate molecule, it is preferred to release them in the pyrophosphorolysis step and/or to adjust the fluid flows through the first zone so that each filled microdroplet generated is separated on average by from 1 to 20 preferably 2 to 10 empty ones. Suitably the microdroplets have a finite volume of less than 500 pL (picolitres), preferably less than 65 pL, more preferably less than 4 pL and even more preferably less than 2 pL. Most preferably of all their volumes are in the range 4 fL (femtolitres) to 4 pL. In one embodiment, the microdroplet flow rate through the device is in the range 50 to 3000 microdroplets per second preferably 100 to 2000.

Thereafter, the microdroplet stream can be microfluidically manipulated and delivered to the microdroplet manipulation zone.

As regards the microdroplet manipulation zone, this is suitably a structure constructed of or defined by first and second composite walls comprised of first and second substrates, first and second conductor layers, a photoactive layer and first and second dielectric layers. In one embodiment this zone comprises a chip or flat cartridge which is hollow and accommodates the microfluidic space. In another, at least the first substrate and first conductor layers are transparent enabling light from the source of electromagnetic radiation (for example multiple laser beams or LED diodes) to impinge directly onto the photoactive layer. In another, the second substrate, second conductor layer and second dielectric layer are transparent so that the same objective can be obtained. In yet another embodiment all these layers are transparent enabling illumination to occur from either side.

Suitably the first and second substrates are made of a material which is mechanically strong for example glass, metal or an engineering plastic. In one embodiment, the substrates may have a degree of flexibility. In yet another embodiment, the first and second substrates have a thickness in the range 100-1000 μm.

The first and second conductor layers are located on one surface of the first and second substrates and are typically very thin; each having a thickness in the range 70 to 250 nm, preferably 70 to 150 nm. In one embodiment, at least one of these layers is made of a transparent conductive material such as Indium Tin Oxide (ITO), a very thin film of conductive metal such as silver or a conducting polymer such as PEDOT or the like. The layers may be formed as a continuous sheet or a series of discrete structures such as wires. Alternatively, the conductor layer may be a mesh of conductive material with the electromagnetic radiation being directed between the interstices of the mesh.

The photoactive layer is suitably comprised of a semiconductor material which can generate localised areas of charge in response to stimulation by the source of electromagnetic radiation. Examples include amorphous silicon in a thickness range from 300 to 1000 nm. In one embodiment the photoactive layer is activated by the application of visible light.

The photoactive layer in the case of the first wall and optionally the conducting layer in the case of the second wall are coated with a dielectric layer which is very thin and typically in the range 120 to 160 nm. The dielectric properties of this layer preferably include a high dielectric strength of $>10^7$ V/m and a dielectric constant of $>3$. In one embodiment, the dielectric layer is selected from high purity alumina or silica, hafnia or thin non-conducting polymer film.

In another version of the device at least the first dielectric layer, preferably both, are coated with an anti-fouling layer to assist in establishing the desired microdroplet/oil/surface contact angle at the various electrowetting locations and additionally to prevent the contents of the microdroplets adhering to the surface and being diminished as the droplet is moved across the device. If the second wall does not comprise a second dielectric layer then the second antifouling layer may applied directly onto to the second conductor layer. For optimum performance the antifouling layer should assist in establishing a contact angle should in the range 50-70° when measured as an air-liquid-surface three-point interface at 25° C. Dependent on the choice of carrier phase the same contact angle of microdroplets in a device filled with an aqueous emulsion will be higher; greater than 100°. In one embodiment, these layer(s) have a thickness of less than 50 nm and are typically a monomolecular layer. In another, these layers are comprised of a polymer of an acrylate ester such as methyl methacrylate or a derivative thereof substituted with hydrophilic groups; e.g. alkoxysilyl. Preferably either or both of the antifouling layers are hydrophobic to ensure optimum performance.

The first and second dielectric layers and therefore the first and second walls define a microfluidic space which is less than 10 μm in depth and in which the microdroplets are contained. In one embodiment, before they are contained in the microdroplet space, the microdroplets have an intrinsic diameter which is more than 10% greater suitably more than 20% greater, than the depth of the microdroplet space. This may be achieved, for example, by providing the device with an upstream inlet, such as a microfluidic orifice where microdroplets having the desired diameter are generated in the carrier medium. By this means, on entering the device the microdroplets are caused to undergo compression leading to enhanced electrowetting performance for certain operations through the addition of surface potential energy above the uncompressed spherical condition of the microdroplets.

In another embodiment, the microfluidic space includes one or more spacers for holding the first and second walls apart to a predetermined depth. Options for spacers include beads or pillars, ridges or the like created from an intermediate resist layer which has been produced by photo-patterning. Various spacer geometries can also be used to define narrow channels, tapered channels or partially enclosed channels which are defined by lines of pillars. By careful design, it is possible to use these structures to aid in the deformation of the microdroplets, to subsequently perform droplet splitting and to carry out operations on the deformed microdroplets.

The depth between the first and second walls affects the level of deformation of the microdroplets; adding or removing surface drag which impedes microdroplet motion. By structuring the device such that the spacing between the first and second walls varies across the device it is possible to have a composite device in which the preferred performance profile is available for different operations; for example such a region can have depth of less than 2 um in regions where 5 µm diameter microdroplets are to be deformed for splitting, and a neighbouring region can have spacing of around 5 µm in which similarly sized microdroplets experience less surface drag and so are able to move at higher speeds.

The first and second walls are biased using a source of A/C power attached to the conductor layers to provide a voltage potential difference therebetween; suitably in the range 10 to 50 volts.

The sequencing device of the present invention further includes a source of electromagnetic radiation having a wavelength in the range 400-1000 nm and an energy higher than the bandgap of the photoexcitable layer. Suitably, the photoactive layer will be activated at electrowetting locations where the incident intensity of the radiation employed is in the range 0.01 to 0.2 $Wcm^{-2}$. The source of electromagnetic radiation is, in one embodiment, highly attenuated and in another pixelated so as to produce corresponding photoexcited regions on the photoactive layer which are also pixelated. By this means corresponding pixelated electrowetting locations on the first dielectric layer are induced. In contrast to the design taught in US20030224528, these points of pixelated electrowetting are not associated with any corresponding permanent structure in the first wall as the conductive cells are absent. As a consequence, in the device of the present invention and absent any illumination, all points on the surface of first dielectric layer have an equal propensity to become electrowetting locations. This makes the device very flexible and the electrowetting pathways highly programmable. To distinguish this characteristic from the types of permanent structure taught in the prior art we have chosen to characterise the electrowetting locations generated in our device as 'ephemeral' and the claims of our application should be construed accordingly.

The optimised structure design taught here is particularly advantageous in that the resulting composite stack has the anti-fouling and contact-angle modifying properties from the coated monolayer (or very thin functionalised layer) combined with the performance of a thicker intermediate layer having high-dielectric strength and high-dielectric constant (such as aluminium oxide or hafnia). The resulting layered structure is highly suitable for the manipulation of very small volume microdroplets, such as those having diameter less than 10 µm, for example in the range 2 to 8, 2 to 6, 2 to 5 or 2 to 4 µm. For these extremely small microdroplets, the performance advantage of having minimal thickness of total non-conducting stack above the photoactive layer is extremely advantageous, as the droplet dimensions start to approach the thickness of the dielectric stack and hence the field gradient across the droplet (a requirement for electrowetting-induced motion) is reduced for the thicker dielectric.

Where the source of electromagnetic radiation is pixelated it is suitably supplied either directly or indirectly using a reflective screen illuminated by light from LEDs. This enables highly complex patterns of ephemeral electrowetting locations to be rapidly created and destroyed in the first dielectric layer thereby enabling the microdroplets to be precisely steered along the electrowetting pathways using closely-controlled electrowetting forces. This is especially advantageous when the aim is to manipulate many thousands of such microdroplets simultaneously along multiple electrowetting pathways. Such electrowetting pathways can be viewed as being constructed from a continuum of virtual electrowetting locations on the first dielectric layer.

The points of impingement of the sources of electromagnetic radiation on the photoactive layer can be any convenient shape including the conventional circular. In one embodiment, the morphologies of these points are determined by the morphologies of the corresponding pixelations and in another correspond wholly or partially to the morphologies of the microdroplets once they have entered the microfluidic space. In one preferred embodiment, the points of impingement and hence the electrowetting locations may be crescent-shaped and orientated in the intended direction of travel of the microdroplet. In another embodiment, the second wall also includes a photoactive layer which enables further ephemeral electrowetting locations to be induced on the second dielectric layer; either by means of the same source of electromagnetic radiation or a second source of the type described herein. Suitably, the electrowetting locations themselves are smaller than the microdroplet surface adhering to the first wall and give a maximal field intensity gradient across the contact line formed between the droplet and the surface dielectric. The addition of a second photoactive layer enables the possibility of transitioning the wetting edge from the upper to the lower surface of the microdroplet manipulation zone, and the targeted application of alternative or additional electrowetting forces to each microdroplet.

In one embodiment, the means for manipulating the points of impingement of the electromagnetic radiation on the photoactive layer is adapted or programmed to produce a plurality of concomitantly-running, for example parallel, first electrowetting pathways on the first and optionally the second dielectric layers. In another embodiment, it is adapted or programmed to also produce a plurality of third electrowetting pathways on the first and optionally the second dielectric layers which intercept with the first electrowetting pathways to create at least one microdroplet-coalescing location where different microdroplets travelling along the different pathways can be caused to coalesce. The first and third electrowetting pathway may intersect at right-angles to each other or at any angle thereto including head-on. This embodiment is especially useful where it is desired to deliver additional components, for example the components of a nucleoside triphosphate capture system and/or various enzymes and other chemical components, into the microdroplets in the microdroplet manipulation zone. In one preferred embodiment, the capture system is based on fluorescence probes which in their unused state are non-fluorescing. Examples of suitable systems include those of our patent applications taught above and in addition our unpublished patent applications EP16187112.4, EP16187493.8 and EP16189791.3 although this list should not be construed as limiting. In yet another embodiment where multiple first, second and third wetting pathways are employed, the means for manipulating the points of impingement is suitably controlled by a microprocessor which not only creates the pathways along which the microdroplets pass but also synchronises the movement of each microdroplet relative to each other one.

The sequencer of the present invention further comprises a detection zone which may be integral with the microdroplet manipulation zone (for example within the chip) or located separately downstream thereof and an associated fluorescence or Raman-scattering system adapted to impinge on the microdroplets. In one preferred embodiment, fluorescence detection derived from fluorophores which are liberated by exonucleolytic digestion or endonucleolytic cleavage is employed. In one embodiment, the detection zone may comprise a surface provided with locations to which the microdroplets are ultimately driven by one or a combination of conventional or optically-mediated EWOD. Such a surface may be profiled with structures such as wells and the like to create final destinations for the microdroplets. In this embodiment, the fluorescence-detection system is configured so that second electromagnetic radiation is caused to impinge on these final destinations to stimulate fluorescence emissions from the microdroplet which is detected by a photodetector or the like. In another embodiment, the detection zone comprises a block of capillary tubes through which each microdroplet is stacked and travels before being interrogated by the fluorescence-detection system at the point of exit.

As regards the fluorescence-detection system, this is comprised of one or more sources of second electromagnetic radiation for example one of more lasers or LEDs to interrogate the contents of each microdroplet and one or more photodetectors or an equivalent devices tuned to the characteristic fluorescence wavelength(s) or wavelength envelope(s) of the various fluorophores employed in the particular capture system being use. Any fluorescence detected by the photodetector(s) thereafter gives rise to and electrical signal which can be processed and analysed in a computer using known algorithms to reveal data characteristic of the sequence of the analyte.

In one embodiment the device of the present invention further includes a central microprocessor and associated computer programs/algorithms for controlling and automating some or all of its various operations.

It will be apparent that the device of the present invention may be used in association with a corresponding sequencing method. Thus, according to a fourth aspect of the present invention there is provided a method of investigating a polynucleotide analyte characterised by comprising the steps of:
  causing an aqueous pyrophosphorolysing medium to contact the analyte immobilised at an attachment site located in a first pathway; thereby allowing the analyte to be progressively pyrophosphorolysed into its constituent nucleoside triphosphates;
  removing the nucleoside triphosphates from around the attachment site in the form of form of a second aqueous medium via a second microfluidic pathway;
  manipulating microdroplets derived from the second aqueous medium in an immiscible carrier medium using an optically-mediated electrowetting device comprised of
    a first composite wall comprised of
      a first transparent substrate;
      a first transparent conductor layer on the substrate having a thickness in the range 70 to 250 nm;
      a photoactive layer activated by electromagnetic radiation in the wavelength range 400-1000 nm on the conductor layer having a thickness in the range 300-1000 nm and
      a first dielectric layer on the photoactive layer having a thickness in the range 120 to 160 nm and
    a second composite wall comprised of
      a second substrate;
      a second transparent conductor layer on the substrate having a thickness in the range 70 to 250 nm and
      optionally a second dielectric layer on the conductor layer having a thickness in the range 25 to 50 nm;
      wherein the exposed surfaces of the first and second dielectric layers are disposed less than 10 um apart to define a microfluidic space adapted to contain microdroplets;
    an A/C source to provide a potential difference across the first and second composite walls connecting the first and second conductor layers;
    at least one source of first electromagnetic radiation having an energy higher than the bandgap of the photoexcitable layer adapted to impinge on the photoactive layer to induce corresponding ephemeral first electrowetting locations on the surface of the first dielectric layer and
    means for manipulating the points of impingement of the electromagnetic radiation on the photoactive layer so as to vary the disposition of the ephemeral electrowetting locations thereby creating at least one first electrowetting pathway along which the microdroplets may be caused to move;
  wherein the microdroplets at some point during the manipulation further comprise some or all of a nucleoside triphosphate, an oligonucleotide capture system comprised of fluorescence probes which in their unused state are non-fluorescing, a polymerase, optionally a ligase and an exonuclease and/or an endonuclease capable of causing the fluorophore(s) to be released from the used capture system in a fluorescing state;
  detecting fluorescence derived from the released fluorophore(s) in each microdroplet when irradiated with a source of electromagnetic radiation.

The analyte may be DNA or RNA of natural or synthetic origin and the capture system chosen will be compatible therewith. The method is especially suitable for sequencing and in one embodiment can advantageously be used with the third aspect of the invention described above.

A device according to the present invention suitable for sequencing polynucleotide DNA analyte is now illustrated by the following Figures and description.

Figure 1:
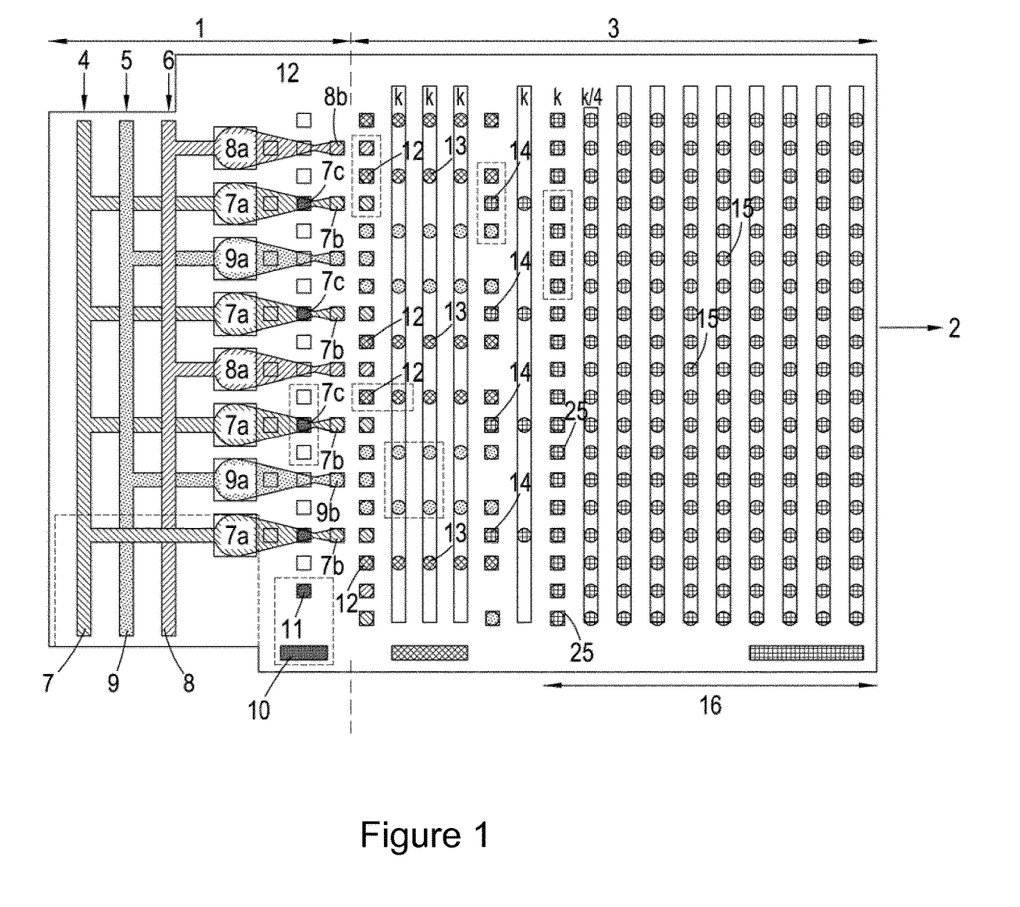

FIG. 1 shows a plan of a microfluidic chip comprised of microdroplet preparation zone 1 and microdroplet manipulation zone 3 integrated into a single chip made of transparent plastic. 1 comprises regions containing fluid 7, 8 and 9 attached to inlets 4, 5 and 6 which respectively introduce into the chip a pyrophosphorolysing stream, an inorganic pyrophosphatase stream and a stream of the various detection chemicals and enzymes required to identify nucleoside triphosphates in accordance with one of our earlier patent applications. These streams are then delivered respectively to orifices 7a, 8a and 9a from which various microdroplets 7b, 8b and 9b are produced (for example using a droplet-dispensing head or by cutting from a larger intermediate droplet). 10 is a reservoir containing paramagnetic-polymer composite microbeads 11 to which are attached a single molecule of the polynucleotide analyte to be sequenced. Each of 11 is transported along electrowetting pathway 12 to a location 7c where it is held and contacted with a stream of 7b. In the process the analyte attached to 11 is progressively pyrophosphorolysed at a rate such that after each 7b is disengaged from 11 it is either empty or contains only one single nucleoside triphosphate molecule. After disengagement, 7b along with microdroplets 8b and 9b, are caused to move to 3 where they are manipulated along various opto-electrowetting paths (defined here by square electrowetting locations 25) at a temperature of 30-40° C. in accordance with the scheme illustrated in FIG. 2. In the process, 7b and 8b are first caused to coalesce at first coalescing points 12 to generate intermediate microdroplets 13 which are thereafter caused to coalesce with 9b at second coalescing points 14 to generate a plurality of streams of final microdroplets 15 which move forward through an incubation region 16 by optoelectrowetting at a temperature in the range 60-75° C. in order to allow the contents to incubate and the necessary chemical and enzymatic reactions to take place. Thereafter, 15 are transported to final locations in detection zone 2 where they are interrogated with light from a LED source and any fluorescence emitted by each microdroplet detected using a photodetector. The output of the photodetector is a data stream corresponding to the sequence of the analyte which can be analysed using known sequencing algorithms.

Figure 2:
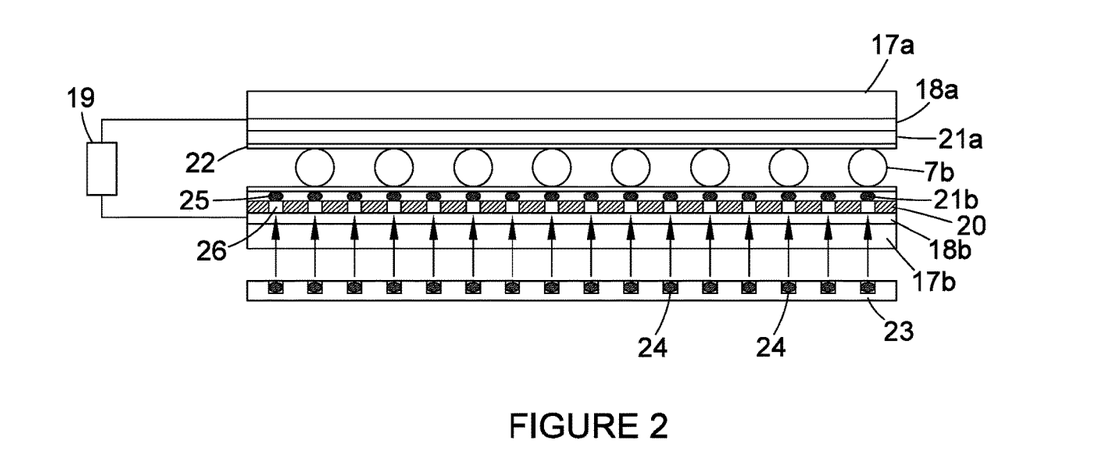

FIG. 2 shows a partial, sectional view of 3 illustrating how the various microdroplets are manipulated 3 comprises top and bottom glass or transparent plastic plates (17a and 17b) each 500 μm thick and coated with transparent layers of conductive Indium Tin Oxide (ITO) 18a and 18b having a thickness of 130 nm. Each of 18a and 18b is connected to an A/C source 19 with the ITO layer on 18b being the ground. 18b is coated with a layer of amorphous silicon 20 which is 800 nm thick. 18a and 20 are each coated with a 160 nm thick layer of high purity alumina or hafnia 21a and 21b which are in turn coated with a monolayer of poly(3-(trimethoxysilyl)propyl methacrylate) 22 to render their surfaces hydrophobic. 21a and 21b are spaced 3 μm apart using spacers (not shown) so that the microdroplets undergo a degree of compression when introduced into the device. An image of a reflective pixelated screen, illuminated by an LED light source 23 is disposed generally beneath 17b and visible light (wavelength 660 or 830 nm) at a level of 0.01 Wcm$^2$ is emitted from each diode 24 and caused to impinge on 20 by propagation in the direction of the multiple upward arrows through 17b and 18b. At the various points of impingement, photoexcited regions of charge 26 are created in 20 which induce modified liquid-solid contact angles in 21b at corresponding electrowetting locations 25. These modified properties provide the capillary force necessary to propel the microdroplets from one point 25 to another. 23 is controlled by a microprocessor (not shown) which determines which of 26 in the array are illuminated at any given time by pre-programmed algorithms. By this means the various microdroplets can be moved along the various pathways shown in FIG. 1 in a synchronised way.

Figure 3:
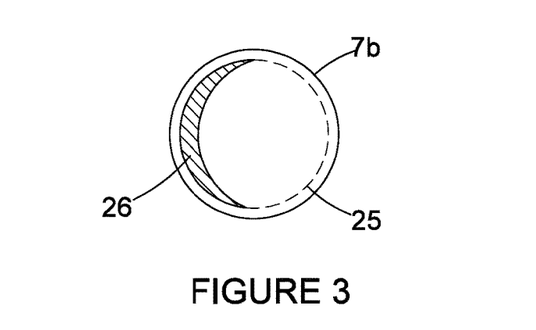

FIG. 3 shows a top-down plan of a typical microdroplet (here 7b) located at a location 25 on 21b with the dotted outline 7' delimiting the extent of touching. In this example, 26 is crescent-shaped in the direction of travel of 7b.

The invention claimed is:

1. A device for manipulating many thousands of microdroplets simultaneously by optically-mediated electrowetting (oEWOD), the device comprising
    a chip comprising a first dielectric layer;
    a reflective screen illuminated by light from LEDs configured to rapidly create and destroy highly complex patterns of ephemeral electrowetting locations or points of impingement of the light in the first dielectric layer thereby enabling the microdroplets to be precisely steered using closely controlled electrowetting forces;
    a microprocessor configured to manipulate the points of impingement in order to create pathways along which the microdroplets pass and further configured to synchronise the movement of each microdroplet relative to each other; and
    a fluorescence or Raman-scattering detection system including a second electromagnetic radiation configured to stimulate fluorescence emissions from the microdroplets; and a photodetector to detect these emissions.

2. The device according to claim 1, wherein the chip further comprises first and second composite walls comprised of first and second substrates, first and second conductor layers, a photoactive layer and a second dielectric layer.

3. The device according to claim 2, wherein the first and second composite walls further comprise first and second antifouling layers on respectively the first and second dielectric layers.

4. The device according to claim 2, wherein a spacer is provided for holding the first and second walls apart to a predetermined depth.

5. The device according to claim 4, wherein the spacer is a pillar.

6. The device according to claim 4, wherein the spacer is a bead.

7. The device according to claim 4, wherein the spacer is a ridge.

8. The device according to claim 4, wherein the spacer is provided by tapered channels.

9. The device according to claim 1, further comprising an A/C power source attached to the conductor layers to provide a voltage potential difference between in the range 10-50V.

\* \* \* \* \*